United States Patent [19]

Björk et al.

[11] 4,366,162
[45] Dec. 28, 1982

[54] ARYL ETHERS OF N-ALKYL-PIPERIDINES AND ACID ADDITION SALTS THEREOF

[75] Inventors: Anders K. K. Björk, Bjärred; Aina L. Abramo, Malmö; Bengt E. S. Kjellberg, Staffanstorp, all of Sweden

[73] Assignee: AB Ferrosan, Malmö, Sweden

[21] Appl. No.: 954,340

[22] Filed: Oct. 25, 1978

[30] Foreign Application Priority Data

Nov. 9, 1977 [GB] United Kingdom ............... 46680/77

[51] Int. Cl.$^3$ .................. A61K 31/445; C07D 211/50
[52] U.S. Cl. .................................... 424/267; 546/221; 546/222
[58] Field of Search ................. 546/221, 222; 424/267

[56] References Cited

U.S. PATENT DOCUMENTS 4,021,564 5/1977 Hernestam et al. ................. 546/221

Primary Examiner—Norma S. Milestone
Attorney, Agent, or Firm—Scully, Scott, Murphy & Presser

[57] ABSTRACT

Aryl ethers of N-alkyl-piperdines having the formula

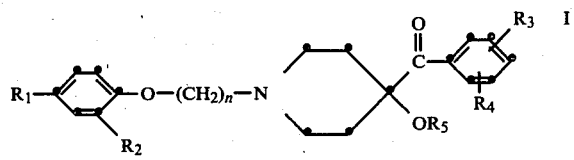

wherein $R_1$ represents hydrogen, halogen including F, Cl and Br, a lower alkanoyl group (e.g. alkanoyl of up to five carbon atoms), an alkenyl group (having three to five carbon atoms) or phenoxy, $R_2$ represents hydrogen, halogen including F, Cl and Br, —CN group, a lower alkoxy group (e.g. alkoxy of up to five carbon atoms), a lower alkanoyl group (e.g. alkanoyl of up to five carbon atoms), an alkenyloxy or alkynyloxy group (having three to five carbon atoms) or a lower alkoxycarbonyl group (e.g. alkoxycarbonyl of up to five carbon atoms), $R_3$ and $R_4$ independently represent hydrogen, halogen including F, Cl and Br, a —CF$_3$ group, a lower alkyl group (e.g. alkyl of up to five carbon atoms) or a lower alkoxy group (e.g. alkoxy of up to five carbon atoms), $R_5$ represents hydrogen or an acyl group with 2-19 carbon atoms and n=3 or 4, and pharmaceutically acceptable acid addition salts. Pharmaceutical compositions containing said substances. Said substances are active in the central nervous system.

14 Claims, No Drawings

ARYL ETHERS OF N-ALKYL-PIPERIDINES AND ACID ADDITION SALTS THEREOF

This invention relates to a novel class of 1-substituted-4-aroyl-4-hydroxypiperidines, acid addition salts thereof, pharmaceutical compositions containing the same, and methods of making and using the same. Said compounds possess a new type of CNS-depressant and antipsychotic properties.

The therapeutic treatment of schizophrenic patients (psychotic) today is by administration of neuroleptic drugs, i.e. chlorpromazine and haloperidol and chemically closely related compounds. Pharmacologically said compounds have about the same properties. Thus, they inhibit amphetamine and apomorphine induced behavioural stereotypies, isolation induced aggressive behaviour, and exploratory behaviour as well as conditioned avoidance responses in different animal species. Many of these effects are thought to depend upon blocking of dopamine receptors in the central nervous system and the idea that schizophrenia is caused by an overactivity in these dopamine neurons has also been forwarded, the so called dopamine hypothesis. However, in recent days this hypothesis has been questioned [JAMA, 239 (4), 291 (1978)] and it is thought that many of the pharmacological tests used to find new neuroleptic compounds do not indicate a neuroleptic effect but are instead indicators of the unwanted side-effects, i.e. neurological and endocrinological disturbances, which in fact are strongly correlated to the blocking of the dopamine receptors caused by the neuroleptics. These tests include the amphetamine- and apomorphineantagonism tests.

It has been discovered that compounds having the general formula

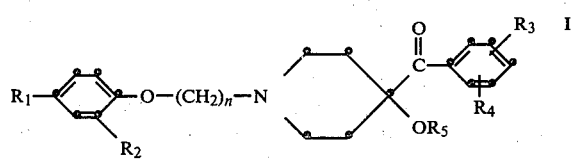

wherein $R_1$ represents hydrogen, halogen including F, Cl and Br, a lower alkanoyl group (e.g. alkanoyl of up to five carbon atoms), an alkenyl group (having three to five carbon atoms) or phenoxy, $R_2$ represents hydrogen, halogen including F, Cl and Br, —CN group, a lower alkoxy group (e.g. alkoxy of up to five carbon atoms), a lower alkanoyl group (e.g. alkanoyl of up to five carbon atoms), an alkenyloxy or alkynyloxy group (having three to five carbon atoms) or a lower alkoxycarbonyl group (e.g., alkoxycarbonyl of up to five carbon atoms), $R_3$ and $R_4$ independently represent hydrogen, halogen including F, Cl and Br, a —$CF_3$ group, a lower alkyl group (e.g. alkyl of up to five carbon atoms) or a lower alkoxy group (e.g. alkoxy of up to five carbon atoms), $R_5$ represents hydrogen or an acyl group with 2–19 carbon atoms and $n=3$ or 4, possess valuable pharmacological properties.

The new compounds of formula I have central nervous system depressing properties like the conventional neuroleptics but lack the strong antidopaminergic properties. Thus, these compounds show low activity in the amphetamine and apomorphine antagonism tests, and consequently the occurence of extrapyramidal side-effects has not been observed in tests performed in monkeys that are preferably used to study these effects.

The new compounds of formula I are potential antipsychotic drugs because they strongly inhibit aggressive behaviour in different kinds of animals. Furthermore, these compounds have no anticholinergic properties; this is important because such effects may counteract the antipsychotic effect and may cause tardive dyskinesias in long term treatment.

The new compounds of formula I also inhibit to a varying degree the noradrenergic and serotoninergic transmission in the brain and, therefore, act to stabilise the balance between these two systems.

According to the process provided by the invention the novel 1-substituted-4-aroyl-4-hydroxypiperidines of the general formula I are prepared according to the following reaction sequence:

by reacting the 4-aroyl-4-hydroxy piperidine of formula II with an alkyl aryl ether of formula III wherein X is halogen, e.g. Cl or Br, or another reactive group, e.g. mesyl or tosyl ester group, to produce a compound of formula I.

The aroyl-4-hydroxypiperidines of formula II which are employed in the method of the invention can be prepared according to the U.S. Pat. No. 4,021,564.

The alkyl aryl ethers of formula III are prepared by alkylation of a phenoxide salt of formula IV

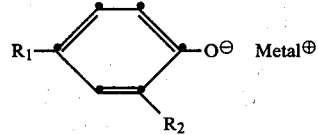

wherein Metal is Na or K, with a bromochloroalkane in a polar solvent, e.g. acetone and the like.

In said reaction the compound of formula II is reacted with a compound of formula III in a suitable solvent, e.g. isobutylacetate, 2-butanone, toluene and the like. The reaction is preferably performed in the presence of an acid binding agent, e.g., sodium carbonate, triethylamine, and the like and advantageously but not necessarily in an autoclave at 75°–150° C.

The subject compound of formula I may be converted to the therapeutically active non-toxic acid addition salt form by treatment with an appropriate acid, e.g. an inorganic acid, such as a hydrohalic acid, especially hydrochloric and hydrobromic acid, or sulfuric acid, nitric acid, phosphoric acid and the like, or an organic acid, such as acetic, propionic, glycolic, lactic, succinic, fumaric, tartaric, citric and the like acids. Conversely, the salt form can be converted by treatment with alkali into the free base form.

The 4-acyloxy compounds of any type I compounds, as set forth in Table III, are formed by treating the 4-hydroxy compounds of type I with a selected carboxylic anhydride using a 4-dialkylaminopyridine as an acylation catalyst. An appropriate tertiary amine is used to bind the acid formed in the reaction. As a reaction medium there may be used a non-protic solvent, excess of the tertiary amine, or excess anhydride.

Conventional types of neuroleptics are potent inhibitors of amphetamine induced behavioural stereotypies. One determines in Sprague Dawley female rats the ability of subcutaneously administered compounds to inhibit compulsory gnawing and chewing responses to a subcutaneous dose of 10 mg/kg of amphetamine administered half an hour after the compound to be tested. The new compounds of formula I are weak antagonists in this test.

All typical chloropromazine-like neuroleptics are powerful antagonists of apomorphine induced emesis in dogs by virtue of their blocking action on the chemoemetic trigger zone. The compounds listed in Table I were administered subcutaneously. The animals were challenged half an hour after subcutaneous administration with a standard dose of 0.06 mg/kg of apomorphine hydrochloride (subcutaneously). This dose of apomorphine induces emesis in all untreated dogs. The new compounds of formula I are weak antagonists in this test.

The isolation induced aggressive behaviour test was used to determine tranquillising activity of the compounds listed in Table I, [S. Garattini and E. B. Sigg, Aggressive Behaviour, 1969]. Male albino mice were used. Tests were conducted 60 minutes after subcutaneous drug administration. The new compounds of formula I are potent in this test.

The ED$_{50}$-values expressed in milligrams per kilogram body weight in the anti-amphetamine test, in the anti-apomorphine test and in the inhibition of aggression test are presented in Table I.

The new compounds of formula I have been found to be devoid of anticholinergic properties but have antihistaminergic properties evaluated from the effects on the acetylcholine (0.02 μg/ml) and histamine (0.2 μg/ml), respectively, induced contraction of guinea pig ileum. They show antiserotoninergic activity evaluated from the effects on serotonin (220 ng/ml) induced contraction of the rat ileum. The ED$_{50}$-values from these tests are summarised in Table II. The ED$_{50}$-values expressed in μg/ml is the dose producing an inhibition of the contraction of 50%.

TABLE I

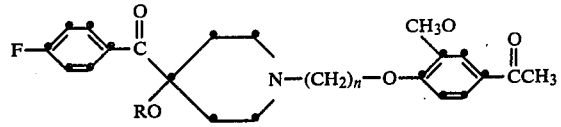

| Compound | R | n | Anti-amphetamine test | Anti-apomorphine test | Inhibition aggression test |
|---|---|---|---|---|---|
| I | H | 3 | 20 | 7,1 | 0,5 |
| II | H | 4 | | | 1,5 |
| III | C$_2$H$_5$CO | 3 | | | 2,0 |
| Chlor- | | | | | |

TABLE I-continued

| Compound | R | n | Anti-amphetamine test | Anti-apomorphine test | Inhibition aggression test |
|---|---|---|---|---|---|
| promazine | | | 1,2 | 0,7 | 0,4 |
| Haloperidol | | | 0,03 | 0,012 | 0,8 |

TABLE II

| Compound | R | n | Anti-cholinergic activity | Anti-histaminic activity | Antiserotoninergic activity |
|---|---|---|---|---|---|
| I | H | 3 | >100 | 0,06 | 0,1 |
| Chlorpromazine | | | 1,7 | 0,03 | 6 |
| Haloperidol | | | 32 | 0,5 | 5 |

The new compounds possess a new type of potent CNS-depressant and antipsychotic properties. They are weak amphetamine-antagonists and have no or little cataleptogenic properties in rats. They inhibit aggression in isolated male mice. Their toxicity is low. They are inhibitors of dopamine-sensitive adenylcyclase. Central depressant and neuroleptic properties have also been observed in monkeys but without any extrapyramidal side-effects.

The compounds may be used in the treatment of various mental disorders such as acute or chronic psychosis, mania or as tranquillisers without or with only few motor disturbances. The new compounds seem to be useful in the treatment of aggressive behaviour in animals, in the development of a natural hierarchy in groups of animals without burst of aggression and in calming of anxious and stressed animals. Some of the compounds have analgesic activity.

The new compounds or their acid addition salts such as the hydrochloride can be administered per os, e.g. in the form of pills or tablets.

For many purposes, a suitable clinical dose is from 10 to 600 mg per day. Naturally the dosage must be adjusted in accordance with the condition, age and weight of the subjects.

The invention also includes compositions suitable for administration to humans and animals comprising the new compounds of the invention or acid addition salts thereof, especially the hydrochlorides, together with an inert diluent or carrier.

Tablets may be prepared by compounding one of the new compounds or an acid addition salt thereof with customary carriers and adjuvants, the following being a suitable table formulation:
1 gm of the hydrochloride of 1-[3-(p-acetyl-o-methoxyphenoxy)-propyl]-4-(p-fluorobenzoyl)-4-hydroxypiperidine
9 gms of potato starch
1 gm of colloidal silica
2.5 gms of a 5% aqueous solution of gelatine
2 gms of talcum
0.2 gms of magnesium stearate This mixture is made up into 100 tablets, i.e. each containing 10 mgs of the active component.

Other galenic formulations, e.g. emulsions, solutions in water or propylene glycol, are also suitable administering possibilities.

The following examples are intended to illustrate, but not to limit the scope of the present invention.

EXAMPLE 1

3-(p-Acetyl-o-methoxyphenoxy)-propyl chloride

To a solution of 88.0 g (0.53 mole) of acetovanillone in 375 ml of acetone was added 69.1 g (0.5 mole) of $K_2CO_3$. The mixture was allowed to reflux for 30 min. A solution of 110.2 g (0.70 mole) of 1-bromo-3-chloropropane in 75 ml of acetone was added dropwise. The mixture was heated at reflux for 20 h. The mixture was filtered and the filtrate concentrated under vacuum. The residual oil was distilled. An oil which weighed 110 g was obtained at 141°–143° C.0.1 mm Hg. The oil crystallised upon standing.

EXAMPLE 2

1-[3-(p-Acetyl-o-methoxyphenoxy)-propyl]-4-(p-fluorobenzoyl)-4-hydroxy-piperidine hydrochloride A stirred mixture of 11.1 g (0.05 mole) of 4-(p-fluorobenzoyl)-4-hydroxy-piperidine, 14.6 g (0.06 mole) of 3-(p-acetyl-o-methoxyphenoxy)-propyl chloride and 25 g of anhydrous sodium carbonate in 350 ml iso-butylacetate was allowed to reflux for 48 h. The mixture was filtered and the filtrate was concentrated under vacuum. The residual oil was converted to the HCl salt. 1-[3-(p-Acetyl-o-methoxyphenoxy)propyl]-4-(p-fluorobenzoyl)-4-hydroxy-piperidine hydrochloride was recrystallised from ethanol. Melting point 160°–162° C. Yield 16.2 g. Said product contained a certain amount of ethanol which can only be removed by extreme means.

EXAMPLE 3

1-[3-(p-Acetyl-o-methoxyphenoxy)-propyl]-4-(p-fluorobenzoyl)-4-octanoyloxypiperidine hydrochloride A mixture of 4.29 g (0.010 mole) of 1-[3-(p-acetyl-o-methoxyphenoxy)-propyl]-4-(fluorobenzoyl)-4-hydroxypiperidine, 27.0 g (0.10 mole) of octanoic anhydride, 1.5 g (0.015 mole) of triethylamine and 0.3 g (0.002 mole) of 4-pyrrolidinopyridine was heated for 3 h at 40° C. Excess anhydride and triethylamine was removed under reduced pressure. The residue was dissolved in ethylacetate and treated with ethanolic HCl. The solid which precipitated was collected by filtration and recrystallised from ethanol giving 3.6 g of 1-[3-(p-acetyl-o-methoxyphenoxy)-propyl]-4-(p-fluorobenzoyl)-4-octanoyloxy-piperidine hydrochloride. Melting point 173°–175° C.

TABLE III

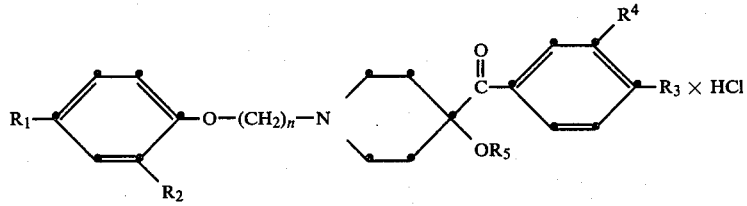

| Compound | $R_1$ | $R_2$ | $R_3$ | $R_4$ | $R_5$ | n | M.p. °C.[a] |
|---|---|---|---|---|---|---|---|
| I | $COCH_3$ | $OCH_3$ | $R_3$ | $R_4$ | $R_5$ | n | 170–171 |
| II | $COCH_3$ | $OCH_3$ | F | H | H | 3 | 160–162 |
| III | $COCH_3$ | $OCH_3$ | F | H | $CH_3CH_2CO$ | 3 | 175–177 |
| IV | $COCH_3$ | $OCH_3$ | F | H | $CH_3(CH_2)_6CO$ | 3 | 173–175 |
| V | $COCH_3$ | $OCH_3$ | F | H | H | 4 | 158–161[b] |
| VI | $COCH_3$ | $OCH_3$ | Cl | H | H | 3 | 173–175 |
| VII | $COCH_3$ | $OCH_3$ | Cl | H | H | 4 | 107–109[c] |
| VIII | $COCH_3$ | $OCH_3$ | Cl | Cl | H | 3 | 156–157 |
| IX | $COCH_3$ | $OCH_3$ | Br | H | H | 3 | 162–164 |
| X | $COCH_3$ | $OCH_3$ | $CH_3$ | H | H | 3 | 169–171 |
| XI | $COCH_3$ | $OCH_3$ | $CH_3$ | H | H | 4 | 191–192 |
| XII | $COCH_3$ | $OCH_3$ | $CH_3$ | $CH_3$ | H | 3 | 110–111[c] |
| XIII | $COCH_3$ | $OCH_3$ | $OCH_3$ | H | H | 3 | 171–172 |
| XIV | $COCH_3$ | $OCH_3$ | H | $CF_3$ | H | 3 | 167–169 |

[a] Melting points are uncorrected
[b] Oxalate
[c] Ethyl alcoholate

We claim:

1. A compound of the general formula

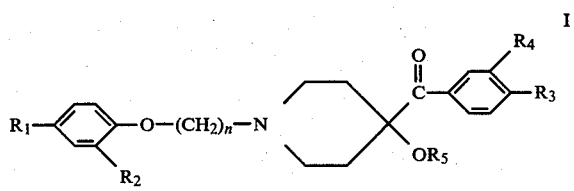

wherein $R_1$ is lower alkanoyl; $R_2$ is lower alkoxy; $R_3$ and $R_4$ independently are hydrogen, F, Cl and Br, $-CF_3$, lower alkyl or lower alkoxy; $R_5$ is hydrogen or an acyl group with 2–19 carbon atoms; and n=3 or 4, and pharmaceutically-acceptable acid addition salts thereof.

2. A compound according to claim 1, wherein $R_1$ is an acetyl group.

3. A compound according to claim 1 or claim 2, wherein $R_2$ is methoxy.

4. The compound according to claim 1 wherein $R_1$ is acetyl, $R_2$ is methoxy, $R_3$, $R_4$ and $R_5$ are each H and n is 3.

5. The compound according to claim 1 wherein $R_1$ is acetyl, $R_2$ is methoxy, $R_3$ is F, $R_4$ and $R_5$ are each H and n is 3.

6. The compound according to claim 1 wherein $R_1$ is acetyl, $R_2$ is methoxy, $R_3$ is F, $R_4$ is H, $P_5$ is propionyl and n is 3.

7. The compound according to claim 1 wherein $R_1$ is acetyl, $R_2$ is methoxy, $R_3$ is F, $R_4$ and $R_5$ are each H and n is 4.

8. The compound according to claim 1 wherein $R_1$ is acetyl, $R_2$ is methoxy, $R_3$ is Cl, $R_4$ and $R_5$ are each H and n is 3.

9. The compound according to claim 1 wherein $R_1$ is acetyl, $R_2$ is methoxy, $R_3$ and $R_4$ are each Cl, $R_5$ is H and n is 3.

10. The compound according to claim 1 wherein $R_1$ is acetyl, $R_2$ is methoxy, $R_3$ is methyl, $R_4$ and $R_5$ are each H and n is 3.

11. A composition for the treatment of mental disorders comprising a compound of formula I as defined in claim 1 in combination with a conventional pharmaceutically acceptable carrier.

12. A pharmaceutical composition according to claim 11 wherein $R_1$ is $COCH_3$; $R_2$ is $OCH_3$; $R_3$ is H, F, Cl, Br, $CH_3$ or $OCH_3$; $R_4$ is H, Cl or $CH_3$; and $R_5$ is H, $CH_3CH_2CO$ or $CH_3(CH_2)_6CO$, and pharmaceutically-acceptable acid addition salts thereof.

13. A method of treating human beings suffering from mental disorders which comprises administering a compound of formula I as defined in claim 1.

14. A method of treating aggressive behaviour in mammals which comprises administering a compound of formula I as defined in claim 1.

* * * * *

UNITED STATES PATENT AND TRADEMARK OFFICE
CERTIFICATE OF CORRECTION

PATENT NO. : 4,366,162
DATED : December 28, 1982
INVENTOR(S) : Bjork, et al.

It is certified that error appears in the above-identified patent and that said Letters Patent are hereby corrected as shown below:

Column 6, Table III, line 1, "$R_3$ $R_4$ $R_5$  n 170-171" should read as --H H H  3 170-171--

Column 6, line 67, claim 6, "$P_5$" should read as --$R_5$--.

Signed and Sealed this

Fifth Day of July 1983

[SEAL]

Attest:

GERALD J. MOSSINGHOFF

Attesting Officer

Commissioner of Patents and Trademarks